US011474107B2

(12) United States Patent
Staker et al.

(10) Patent No.: US 11,474,107 B2
(45) Date of Patent: Oct. 18, 2022

(54) DIGITAL ANALYSIS OF MOLECULAR ANALYTES USING ELECTRICAL METHODS

(71) Applicant: Apton Biosystems, Inc., Pleasanton, CA (US)

(72) Inventors: Bryan P. Staker, San Ramon, CA (US); Niandong Liu, San Ramon, CA (US); Bart Lee Staker, Poulsbo, WA (US); Michael David McLaughlin, San Jose, CA (US)

(73) Assignee: APTON BIOSYSTEMS, INC., Pleasanton, CA (US)

( * ) Notice: Subject to any disclaimer, the term of this patent is extended or adjusted under 35 U.S.C. 154(b) by 0 days.

(21) Appl. No.: 17/696,631

(22) Filed: Mar. 16, 2022

(65) Prior Publication Data
US 2022/0206006 A1    Jun. 30, 2022

Related U.S. Application Data

(63) Continuation of application No. 17/178,203, filed on Feb. 17, 2021, which is a continuation of application No. 14/912,883, filed as application No. PCT/US2014/052186 on Aug. 21, 2014, now abandoned.

(60) Provisional application No. 61/868,988, filed on Aug. 22, 2013.

(51) Int. Cl.
| | | |
|---|---|---|
| G01N 33/58 | (2006.01) | |
| G01N 27/414 | (2006.01) | |
| C12Q 1/6837 | (2018.01) | |
| C12Q 1/6825 | (2018.01) | |
| C12Q 1/6804 | (2018.01) | |
| C40B 20/04 | (2006.01) | |

(52) U.S. Cl.
CPC .......... *G01N 33/58* (2013.01); *C12Q 1/6804* (2013.01); *C12Q 1/6825* (2013.01); *C12Q 1/6837* (2013.01); *G01N 27/4145* (2013.01); *C40B 20/04* (2013.01); *G01N 2458/10* (2013.01)

(58) Field of Classification Search
None
See application file for complete search history.

(56) References Cited

U.S. PATENT DOCUMENTS

| | | | |
|---|---|---|---|
| 5,302,509 A | 4/1994 | Cheeseman | |
| 5,494,810 A | 2/1996 | Barany et al. | |
| 5,763,594 A | 6/1998 | Hiatt et al. | |
| 6,103,474 A | 8/2000 | Dellinger et al. | |
| 6,214,987 B1 | 4/2001 | Hiatt et al. | |
| 6,232,465 B1 | 5/2001 | Hiatt et al. | |
| 6,654,505 B2 | 11/2003 | Bridgham et al. | |
| 6,852,487 B1 | 2/2005 | Barany et al. | |
| 7,057,026 B2 | 6/2006 | Barnes et al. | |
| 7,122,319 B2 | 10/2006 | Liu et al. | |
| 7,769,548 B2 | 8/2010 | Garcia | |
| 7,838,302 B2 | 11/2010 | Zhuang et al. | |
| 7,948,015 B2 | 5/2011 | Rothberg et al. | |
| 7,960,104 B2 | 6/2011 | Drmanac et al. | |
| 8,149,418 B2 | 4/2012 | Tearney et al. | |
| 8,158,346 B2 | 4/2012 | Balasubramanian et al. | |
| 8,175,452 B1 | 5/2012 | Staker et al. | |
| 8,428,454 B2 | 4/2013 | Staker et al. | |
| 8,676,013 B2 | 3/2014 | Bouma et al. | |
| 9,193,998 B2 | 11/2015 | Khurana et al. | |
| 10,378,053 B2 | 8/2019 | Staker et al. | |
| 10,510,435 B2 | 12/2019 | Cai et al. | |
| 10,829,816 B2 | 11/2020 | Staker et al. | |
| 2002/0086322 A1 | 7/2002 | Yu et al. | |
| 2003/0118595 A1 | 6/2003 | Niemeyer et al. | |
| 2003/0207300 A1 | 11/2003 | Matray et al. | |
| 2003/0215862 A1 | 11/2003 | Parce et al. | |
| 2005/0049796 A1 | 3/2005 | Webb et al. | |
| 2005/0153320 A1 | 7/2005 | Herron et al. | |
| 2005/0250094 A1 | 11/2005 | Storhoff et al. | |
| 2006/0014172 A1 | 1/2006 | Muller et al. | |
| 2008/0018898 A1 | 1/2008 | Gunstream et al. | |
| 2008/0161194 A1 | 7/2008 | Turner et al. | |

(Continued)

FOREIGN PATENT DOCUMENTS

| | | |
|---|---|---|
| BY | 4655 C1 | 9/2002 |
| CN | 1584592 A | 2/2005 |

(Continued)

OTHER PUBLICATIONS

Non-Final Office Action received for U.S. Appl. No. 14/912,883, dated Aug. 13, 2019, 8 pages.

Tuerk et al. (Aug. 3, 1990) "Systematic Evolution of Ligands by Exponential Enrichment: RNA Ligands to Bacteriophage T4 DNA Polymerase", Science, 249(4968):505-510.

(Continued)

*Primary Examiner* — Christopher M Gross

(74) *Attorney, Agent, or Firm* — Mintz, Levin, Cohn, Ferris, Glovsky and Popeo, P.C.

(57) ABSTRACT

Electrical detection methods are used to identify and further characterize single-molecule target analytes such as proteins and nucleic acids. A composition including a probe region and a tail region is contacted with a target analyte. The probe region specifically binds to the target analyte. The tail region is coupled to the probe region, and includes a nucleic acid template for polynucleotide synthesis. When conditions are such that polynucleotide synthesis occurs along the tail region, one hydrogen ion is released for every nucleotide that is incorporated into the tail region. A transistor such as an ISFET detects and measures changes in ion concentration, and these measurements can be used to identify the tail region and thus characterize the corresponding target analyte.

20 Claims, 3 Drawing Sheets

(56) References Cited

U.S. PATENT DOCUMENTS

| | | | |
|---|---|---|---|
| 2009/0317810 | A1 | 12/2009 | Lofton-day et al. |
| 2010/0301398 | A1 | 12/2010 | Rothberg et al. |
| 2011/0009296 | A1 | 1/2011 | Kain et al. |
| 2011/0071048 | A1 | 3/2011 | Oshima |
| 2011/0165559 | A1 | 7/2011 | Lane et al. |
| 2012/0020537 | A1 | 1/2012 | Garcia et al. |
| 2012/0052490 | A1 | 3/2012 | Eid et al. |
| 2012/0307121 | A1 | 12/2012 | Lu et al. |
| 2013/0265459 | A1 | 10/2013 | Duparre et al. |
| 2015/0330974 | A1 | 11/2015 | Staker et al. |
| 2017/0152554 | A1 | 6/2017 | Drmanac et al. |
| 2019/0276886 | A1 | 9/2019 | Skinner et al. |
| 2019/0323080 | A1 | 10/2019 | Staker et al. |
| 2020/0140933 | A1 | 5/2020 | Staker et al. |
| 2021/0325397 | A1 | 10/2021 | Staker et al. |

FOREIGN PATENT DOCUMENTS

| | | | |
|---|---|---|---|
| CN | 1653480 | A | 8/2005 |
| CN | 101865843 | A | 10/2010 |
| CN | 101865843 | B | 5/2012 |
| EP | 1388587 | A4 | 12/2006 |
| EP | 2251435 | A1 | 11/2010 |
| JP | 2002524739 | A | 8/2002 |
| JP | 2007536528 | A | 12/2007 |
| JP | 2008249711 | A | 10/2008 |
| WO | 9967641 | A2 | 12/1999 |
| WO | 9967641 | A3 | 3/2000 |
| WO | 0168912 | A2 | 9/2001 |
| WO | 2005113817 | A9 | 8/2006 |
| WO | 2007097754 | A1 | 8/2007 |
| WO | 2008033167 | A2 | 3/2008 |
| WO | 2011137183 | A1 | 11/2011 |
| WO | 2012031011 | A1 | 3/2012 |
| WO | 2014078855 | A1 | 5/2014 |
| WO | 2015027112 | A1 | 2/2015 |
| WO | 2016134191 | A1 | 8/2016 |
| WO | 2016156845 | A1 | 10/2016 |
| WO | 2017223041 | A1 | 12/2017 |
| WO | 2018161013 | A1 | 9/2018 |
| WO | 2018170518 | A1 | 9/2018 |
| WO | 2018175402 | A1 | 9/2018 |

OTHER PUBLICATIONS

Song et al. (Feb. 2008) "Aptamer-Based Biosensors", Trends in Analytical Chemistry, 27(2):108-117.
Sbovodova et al. (Aug. 2012) "Comparison of different methods for generation of single-stranded DNA for SELEX processes", Analytical Bioanalytical Chemistry, 404(3):835-842.
Rotman B. (1961) "Measurement of Activity of Single Molecules of Beta-D-Galactosidase", Proc Natl Acad Sci U S A, 47(12):1981-1991.
Riley et al. (1996) "Reed-Solomon Codes", https://www.cs.cmu.edu/-guyb/realworld/reedsolomon/reedsolomoncodes.html, 6 pages.
Moerner et al. (2003) "Methods of Single-Molecule Fluorescence Spectroscopy and Microscopy", Review of Scientific Instruments, 74(8):3597-3619.
Liu et al. (2012) "Comparison of Next-Generation Sequencing Systems", J Biomed Biotechnol, 251364(11 pages).
Final Office Action received for U.S. Appl. No. 14/443,655, dated Jun. 12, 2018, 15 pages.
Final Office Action received for U.S. Appl. No. 14/443,655, dated Jun. 25, 2019, 37 pages.
Final Office Action received for U.S. Appl. No. 14/443,655, dated Mar. 9, 2017, 27 pages.
(2010) Illumina Sequencing Technology, Technology Spotlight: Illumina® Sequencing, Illumina, Inc., 5 pages.
International Preliminary Report on Patentability for PCT Application No. PCT/US2013/070797, dated Jan. 16, 2015, 13 pages.
International Preliminary Report on Patentability for PCT Application No. PCT/US2014/052186, dated Sep. 21, 2015, 33 pages.
International Preliminary Report on Patentability for PCT Application No. PCT/US2018/023310, dated Sep. 24, 2019, 19 pages.
International Search Report and Written Opinion for PCT Patent Application No. PCT/US2013/070797, dated Feb. 21, 2014, 16 pages.
International Search Report and Written Opinion for PCT Patent Application No. PCT/US2014/052186, dated Dec. 17, 2014, 16 pages.
International Search Report and Written Opinion for PCT Patent Application No. PCT/US2019/051796, dated Jan. 3, 2020, 10 pages.
International Search Report and Written Opinion for PCT Patent Application No. PCT/US2018/023187, dated May 31, 2018, 3 pages.
International Search Report and Written Opinion for PCT Patent Application No. PCT/US2018/023310, dated Sep. 4, 2018, 28 pages.
Toumazou, et al. (Jun. 9, 2013) "Simultaneous DNA Amplification and Detection Using a PH-sensing Semiconductor System", Nature Methods, 10(7):(641-646) 23 pages.
Levy et al. (2016) "Advancements in Next-Generation Sequencing", Annu Rev Genomics Hum Genet, 17:95-115.
Non-Final Office Action received for U.S. Appl. No. 14/443,655, dated Nov. 14, 2016, 19 pages.
Non-Final Office Action received for U.S. Appl. No. 14/443,655, dated Oct. 18, 2017, 26 pages.
Non-Final Office Action received for U.S. Appl. No. 14/912,883, dated Apr. 3, 2019, 10 pages.
Final Office Action received for U.S. Appl. No. 14/912,883, dated Jan. 3, 2020, 10 pages.
Non-Final Office Action received for U.S. Appl. No. 15/925,656, dated Sep. 27, 2018, 24 pages.
Cho et al. (Mar. 30, 2006) "Optimization of Aptamer Microarray Technology for Multiple Protein Targets", Analytica Chimca Acta, 564(1):82-90.
Drmanac et al. (Jan. 1, 2010) "Human Genome Sequencing Using Unchained Base Reads on Self-Assembling DNA Nanoarrays", Science, 327(5961):78-81.
Gavrilovic et al. (2009) "Quantification of Colocalization and Cross-Tk Based on Spectral Angles", Journal of Microscopy, 234(3)311-324.
Gunderson et al. (May 2004) "Decoding Randomly Ordered DNA Arrays", Genome Research, 14(5):870-877.
Guo et al. (Jul. 8, 2008) "Four-Color DNA Sequencing With 3'-O-Modified Nucleotide Reversible Terminators and Chemically Cleavable Fluorescent Dideoxynucleotides", Proceedings of the National Academy of Sciences of the United States of America, 105(27):9145-9150.
(2001) CAS Registry No. 361411-90-7.
Hager et al. (2017) "Arrays of Individual DNA Molecules on Nanopatterned Substrates", Scientific Reports, 7:42075 (9 pages).
Ju et al. (Dec. 26, 2006) "Four-color DNA Sequencing by Synthesis Using Cleavable Fluorescent Nucleotide Reversible Terminators", Proceedings of the National Academy of Sciences of the United States of America, 103(52):19635-19640.
Kao et al. (2009) "BayesCall: A Model-Based Base-Cling algorithm for High-Throughput Short-Read Sequencing", Genome Research, 19(10):1884-1895.
Kumar et al. (2012) "Peg-Labeled Nucleotides and Nanopore Detection for Single Molecule DNA Sequencing by Synthesis", Scientific Reports, 2:684(8 pages).
Lee et al. (Sep. 7, 2009) "Ion-Sensitive Field-Effect Transistor for Biological Sensing", Sensors, 9:7111-7131.
Levene et al. (Jan. 31, 2003) "Zero-Mode Waveguides for Single-Molecule Analysis at High Concentrations.", Science, 299:682-686.
(2001) Gen Bank accession No. BH 156534 database entry.
(2002) Gen Bank Accession No. BU588905.
(2002) Gen Bank Accession No. BU851949.
Guo et al. (Jul. 8, 2008) "Supporting Information for Four-Color DNA Sequencing With 3'-O-Modified Nucleotide Reversible Terminators and Chemically Cleavable Fluorescent Dideoxynucleotides", Proceedings of the National Academy of Sciences of the United States of America, 105(27):9145-9150.

(56) References Cited

OTHER PUBLICATIONS

International Preliminary Report on Patentability for PCT Application No. PCT/US2018/023187, dated Sep. 26, 2019, 27 pages.

DIGITAL ANALYSIS OF MOLECULAR ANALYTES USING ELECTRICAL METHODS

CROSS-REFERENCE TO RELATED APPLICATIONS

This application is a continuation application of U.S. patent application Ser. No. 17/178,203, filed Feb. 17, 2021, which is a continuation of application of U.S. patent application Ser. No. 14/912,883, filed Feb. 18, 2016, now abandoned, which is a National Stage Application of International Pat. Application No. PCT/US2014/052186, filed Aug. 21, 2014, which claims priority to U.S. Provisional Application No. 61/868,988, filed on Aug. 22, 2013, which is incorporated by reference herein in its entirety. This application also incorporates by reference in their entirety U.S. Provisional Application No. 61/728,067 and International Pat. Application No. PCT/US2013/070797.

TECHNICAL FIELD

This disclosure relates compositions and methods useful for the electrical detection of molecules, and more specifically, to the use of digitized electrical signals and the use of error correction protocols to characterize complex mixtures of target analytes.

DESCRIPTION OF THE RELATED ART

Multiple molecular and biochemical approaches are available for molecular analyte identification and quantification. Examples include commonly used nucleic acid-based assays such as qPCR (quantitative polymerase chain reaction) and DNA microarray, and protein-based approaches such as immunoassay and mass spectrometry. However, various limitations exist in current analyte analysis technologies. For example, current methods have limitations of sensitivity, especially where analytes are present in biological samples at low copy numbers or in low concentrations. Most nucleic acid quantification technologies involve sample amplification for higher sensitivity. However, amplification techniques introduce biases and inaccuracies into the quantification. Moreover, amplification is not possible for protein and peptides. Due to lack of sensitivity, approaches for detection and quantification often require relatively large sample volumes.

Current methods are also limited in their capacity for identification and quantification of a large number of analytes. Quantification of all of mRNA and proteins in a sample requires high multiplexity and large dynamic range. In addition, current technologies lack of capability to detect and quantify nucleic acids and proteins simultaneously.

Current methods often generate errors during analyte detection and quantification due to conditions such as weak signal detection, false positives, and other mistakes. These errors may result in the misidentification and inaccurate quantification of analytes.

Therefore, methods and systems are needed for analyte analysis that allows for high sensitivity with small sample volume, high multiplexity, large dynamic range and the ability to detect protein and nucleic acid molecules in a single assay. Furthermore, methods of error correction to correct for analyte detection errors are needed. The present invention addresses these and other limitations of the prior art.

BRIEF DESCRIPTIONS OF THE DRAWINGS

The disclosed embodiments have other advantages and features which will be more readily apparent from the following detailed description of the invention and the appended claims, when taken in conjunction with the accompanying drawings, in which:

FIG. (or "Fig.") 1 illustrates examples of target analytes immobilized on a substrate and specifically bound to compositions, according to an embodiment.

SUMMARY

Figure 1:
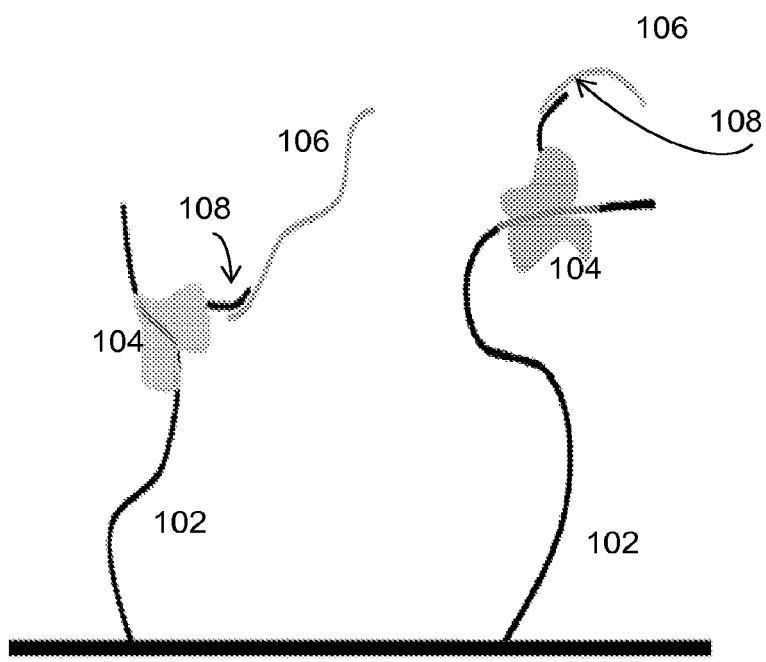

The invention provides a composition, comprising: a probe region, wherein the probe region is configured to specifically bind to a target analyte; a tail region, the tail region comprising a homopolymeric base region comprising at least 25 consecutive nucleotides; and optionally a linker region located between the probe region and the tail region, wherein the linker region comprises a nucleotide sequence configured to specifically bind to a portion of the tail region, and wherein the probe region and the tail region each comprises a separate nucleic acid molecule when the optional linker region is present.

The invention also provides a composition, comprising: a probe region, wherein the probe region is configured to specifically bind to a target analyte; and at least one linker region attached to the probe region, wherein the linker region comprises a nucleotide sequence configured to specifically bind to a portion of at least one tail region, the tail region comprising a homopolymeric base region comprising at least 25 consecutive nucleotides, wherein the probe region and the tail region each comprises a separate nucleic acid molecule. In one embodiment, the composition further comprises at least one tail region, wherein a portion of each tail region is configured to specifically bind to a distinct linker region.

In an embodiment, the tail region and the probe region of a composition are covalently linked through a nucleic acid backbone. In another embodiment, the tail region further comprises one or more nucleotides comprising one or more bases that are distinct from the bases within the homopolymeric base region. In another embodiment, the linker region is configured to specifically bind to portions of multiple tail regions. In a further embodiment, the homopolymeric base region comprises a poly-A tail, a poly-T tail, a poly-C tail, or a poly-G tail. In yet another embodiment, the homopolymeric base region comprises at least 100 or 200 consecutive nucleotides. In some embodiments, the target analyte comprises a protein, a peptide, or a nucleic acid. In other embodiments, the probe region comprises a protein, a peptide, a nucleic acid, or an antibody. In other embodiments, the linker region sequence comprises at least 10 nucleotides, or 20-25 nucleotides.

In one embodiment, the tail region further comprises: a nucleotide adjacent to the homopolymeric base region, wherein the nucleotide comprises a base that is distinct from the bases within the homopolymeric base region; a second homopolymeric base region adjacent to the nucleotide, wherein the second homopolymeric base region comprises bases that are different from the nucleotide base; and optionally a plurality of additional homopolymeric base regions each separated from an adjacent homopolymeric base region, by an intervening nucleotide, wherein the intervening nucleotide base is different from the bases of each adjacent homopolymeric base region.

In another embodiment, each homopolymeric base region comprises the same base. In another embodiment, the nucleotide and each optional intervening nucleotide comprise the same base. In a separate embodiment, a library comprising a plurality of compositions according to claim 15, wherein (1) each probe region is associated with a plurality of linker regions, and (2) each linker region specifically binds to a portion of a distinct tail region. In a further embodiment, the lengths of all of the tail regions in the library are constant.

The invention also provides methods of characterizing at least one target analyte, comprising: obtaining a plurality of ordered tail region sets, each of the ordered tail region sets comprising one or more tail regions of any of claims 1 and 3-18, and directed to a defined subset of N distinct target analytes, wherein the N distinct target analytes are immobilized on spatially separate regions of a substrate; contacting the N distinct target analytes with the probe regions of any of claims 1-18 under conditions designed to promote specific binding of the probe regions of the probe regions to one or more of the immobilized N distinct target analytes; performing at least M cycles, wherein the performing comprises: (1) if the tail regions are not covalently attached to probe regions, a hybridization step comprising contacting the bound probe regions with the tail regions, wherein each tail region specifically binds to a linker region of a probe region; (2) a synthesis step, the synthesis step comprising contacting the bound tail regions with a reaction mixture comprising reagents and under conditions that result in synthesis of a polynucleotide strand using the tail region as a template; and (3) a stripping step, the stripping step comprising stripping the tail regions or the probe regions from the N distinct target analytes; detecting during each of the at least M cycles a plurality of output signals from the spatially separate regions of the substrate; and determining from the detected plurality of output signals at least K bits of information per cycle for one or more of the N distinct target analytes, wherein the at least K bits of information are used to determine L total bits of information, wherein K×M=L bits of information and L>log 2 (N), and wherein the L bits of information are used to identify one or more of the N distinct target analytes.

In an embodiment, $L > \log_2(N)$, and L comprises bits of information used for correcting errors in the plurality of signals. In another embodiment, $L > \log_2(N)$, and L comprises bits of information that are ordered in a predetermined order. In a further embodiment, the predetermined order is a random order. In another embodiment, $L > \log_2(N)$, and L comprises bits of information used for determining an identification code for each of the N distinct target analytes. In a separate embodiment, $L > \log_2(N)$, and L comprises bits of information comprising a key for decoding an order of the ordered tail region sets for each cycle in the at least M cycles. In a further embodiment, a key decodes the identity of one or more of the N distinct analytes. In another embodiment, the L bits of information determined for an N target analyte are compared with an expected bits of information for provided by a key, wherein the comparison is used to determine an identity of the N target analyte. In another embodiment, the number of ordered tail region sets is based on the number of N distinct target analytes.

In one embodiment, the plurality of output signals is digitized to expand a dynamic range of detection of the plurality of signals. In another embodiment, the methods of the invention are computer implemented. In a separate embodiment, the L bits of information can be used to determine an error correction for the plurality of output signals. In a further embodiment, the error correction comprises using a Reed-Solomon Code. In another embodiment, the aforementioned substrate contains at least one transistor that detects the plurality of output signals. In a further embodiment, the transistor is an ion-sensitive field-effect transistor (ISFET) structure.

The invention also provides kits for characterizing at least one target analyte, comprising: a plurality of probe region containers, each probe region container holding a distinct molecule comprising the probe region and the linker region of claim 1; a plurality of ordered tail region containers, each tail region container holding a distinct nucleic acid molecule comprising the tail region of claim 1; a reaction mixture container holding a reaction mixture comprising enzymes and polynucleotides used for synthesizing a polynucleotide strand template from one of the tail regions; and instructions for use comprising instructions for contacting the target analyte with the contents of at least one probe region container, or a portion thereof, the contents of at least one tail region container, or a portion thereof, and the contents of the reaction mixture container, or a portion thereof, under conditions that result in the synthesis of a polynucleotide strand reaction product.

The invention also provides kits for characterizing at least one target analyte, comprising: a plurality of composition containers, each composition container holding a distinct composition of any of claims 1-18; a reaction mixture container holding a reaction mixture comprising enzymes and polynucleotides used for synthesizing a polynucleotide strand template from one of the tail regions if a tail region is present; and instructions for use comprising instructions for contacting the target analyte with the contents of at least one probe region container, or a portion thereof, and the contents of the reaction mixture container, or a portion thereof, under conditions that result in the synthesis of a polynucleotide strand reaction product.

In one embodiment, the kits further comprise: instructions for performing at least M cycles, wherein the performing comprises: (1) if the tail regions are not covalently attached to probe regions, a hybridization step comprising contacting the bound probe regions with the tail regions, wherein each tail region specifically binds to a linker region of a probe region; (2) a synthesis step, the synthesis step comprising contacting the bound tail regions with a reaction mixture comprising reagents and under conditions that result in synthesis of a polynucleotide strand using the tail region as a template; and (3) a stripping step, the stripping step comprising stripping the tail regions or the probe regions from the N distinct target analytes; instructions for detecting during each of the at least M cycles a plurality of output signals from the spatially separate regions of the substrate; and instructions for determining from the plurality of signals at least K bits of information per cycle for one or more of the N distinct target analytes, wherein the at least K bits of information are used to determine L total bits of information, wherein K×M=L bits of information and $L \geq \log_2(N)$, and wherein the L bits of information are used to determine a presence or an absence of one or more of the N distinct target analytes.

In an embodiment, $L > \log_2(N)$. In another embodiment, the instructions further comprise determining an identification of each of the N distinct target analytes using the L bits of information, wherein L comprises bits of information for target identification. In a separate embodiment, the instructions further comprise determining an order of the plurality of ordered probe reagent sets using the L bits of information, wherein L comprises bits of information that are ordered in a predetermined order. In a further embodiment, the predetermined order is a random order. In another embodiment, the instructions further comprise using a key for decoding an order of the plurality of ordered probe reagent sets.

DETAILED DESCRIPTION

The figures and the following description relate to various embodiments of the invention by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Definitions

A "target analyte" or "analyte" refers to a molecule, compound, substance or component that is to be identified, quantified, and otherwise characterized. A target analyte can be a polypeptide, a protein (folded or unfolded), an oligonucleotide molecule (RNA or DNA), a fragment thereof, or a modified molecule thereof, such as a modified nucleic acid. Generally, a target analyte can be at any of a wide range of concentrations (e.g., from the mg/mL to ag/mL range), in any volume of solution (e.g., as low as the picoliter range). For example, samples of blood, serum, formalin-fixed paraffin embedded (FFPE) tissue, saliva, or urine could contain various target analytes. The target analytes are recognized by probes, which are used to identify and quantify the target analytes using electrical or optical detection methods.

Modifications to a target protein, for example, can include post-translational modifications, such as attaching to a protein other biochemical functional groups (such as acetate, phosphate, various lipids and carbohydrates), changing the chemical nature of an amino acid (e.g. citrullination), or making structural changes (e.g. formation of disulfide bridges). Examples of post-translational modifications also include, but are not limited to, addition of hydrophobic groups for membrane localization (e.g., myristoylation, palmitoylation), addition of cofactors for enhanced enzymatic activity (e.g., lipolyation), modifications of translation factors (e.g., diphthamide formation), addition of chemical groups (e.g., acylation, alkylation, amide bond formation, glycosylation, oxidation), sugar modifications (glycation), addition of other proteins or peptides (ubiquination), or changes to the chemical nature of amino acids (e.g., deamidation, carbamylation).

In other embodiments, target analytes are oligonucleotides that have been modified. Examples of DNA modifications include DNA methylation and histone modification. In yet other embodiments, target analytes are small molecules (such as steroids), atoms, or other compounds.

A "probe" as used herein refers to a molecule that is capable of binding to other molecules (e.g., oligonucleotides comprising DNA or RNA, polypeptides or full-length proteins, etc.), cellular components or structures (lipids, cell walls, etc.), or cells for detecting or assessing the properties of the molecules, cellular components or structures, or cells. The probe comprises a structure or component that binds to the target analyte. Examples of probes include, but are not limited to, an aptamer, an antibody, a polypeptide, an oligonucleotide (DNA, RNA), or any combination thereof. Antibodies, aptamers, oligonucleotide sequences and combinations thereof as probes are also described in detail below.

The probe can comprise a tag that is used to detect the presence of the target analyte. The tag can be is directly or indirectly bound to, hybridizes to, conjugated to, or covalently linked to the target analyte binding component. In some embodiments, the tag is a detectable label, such as a fluorescent molecule or a chemiluminescent molecule. In other embodiments, the tag comprises an oligonucleotide sequence that has a homopolymeric base region (e.g., a poly-A tail). The probe can be detected electrically, optically, or chemically via the tag.

As used herein, the term "tag" refers to a molecule capable of detecting a target analyte). The tag can be an oligonucleotide sequence that has a homopolymeric base region (e.g., a poly-A tail). In other embodiments, the tag is a label, such as a fluorescent label. The tag can comprise, but is not limited to, a fluorescent molecule, chemiluminescent molecule, chromophore, enzyme, enzyme substrate, enzyme cofactor, enzyme inhibitor, dye, metal ion, metal sol, ligand (e.g., biotin, avidin, streptavidin or haptens), radioactive isotope, and the like. The tag can be directly or indirectly bound to, hybridizes to, conjugated to, or covalently linked to the probe.

A "protein" or "polypeptide" or "peptide" refers to a molecule of two or more amino acids, amino acid analogs, or other peptidomimetics. The protein can be folded or unfolded (denatured). The polypeptide or peptide can have a secondary structure, such as an α-helix, β sheet, or other conformation. As used herein, the term "amino acid" refers to either natural and/or unnatural or synthetic amino acids, including glycine and both the D or L optical isomers, and amino acid analogs and peptidomimetics. A peptide may be two or more amino acids in length. Longer length peptides are often referred to as polypeptides. A protein can refer to full-length proteins, analogs, and fragments thereof are encompassed by the definition. The terms also include postexpression modifications of the protein or polypeptide, for example, glycosylation, acetylation, phosphorylation and the like. Furthermore, as ionizable amino and carboxyl groups are present in the molecule, a particular polypeptide may be obtained as an acidic or basic salt, or in neutral form. A protein or polypeptide may be obtained directly from the source organism, or may be recombinantly or synthetically produced.

Proteins can be identified and characterized by a peptide sequence, side-chain modifications, and/or its tertiary structure. Side-chain modifications include phosphorylation, acetylation, sugars, etc. Phosphorylation of hydroxyl groups from serine, threonine and tyrosine amino acids are particularly important modifications of interest.

The term "in vivo" refers to processes that occur in a living organism.

The term "mammal" as used herein includes both humans and non-humans and include but is not limited to humans, non-human primates, canines, felines, murines, bovines, equines, and porcines.

"Sample" as used herein includes a specimen, culture, or collection from a biological material. Samples may be derived from or taken from a mammal, including, but not limited to, humans, monkey, rat, or mice. Samples may be include materials such as, but not limited to, cultures, blood, tissue, formalin-fixed paraffin embedded (FFPE) tissue, saliva, hair, feces, urine, and the like. These examples are not to be construed as limiting the sample types applicable to the present invention.

A "bit" as used herein refers to a basic unit of information in computing and digital communications. A bit can have only one of two values. The most common representation of these values are 0 and 1. The term bit is a contraction of binary digit. In one example, a system that uses 4 bits of information can create 16 different values. All single digit hexadecimal numbers can be written with 4 bits. Binary-coded decimal is a digital encoding method for numbers using decimal notation, with each decimal digit represented by four bits. In another example, a calculation using 8 bits, there are $2^8$ (or 256) possible values.

TABLE 1

Example bit values

| Binary | Octal | Decimal | Hexadecimal |
| --- | --- | --- | --- |
| 0000 | 0 | 0 | 0 |
| 0001 | 1 | 1 | 1 |
| 0010 | 2 | 2 | 2 |
| 0011 | 3 | 3 | 3 |
| 0100 | 4 | 4 | 4 |
| 0101 | 5 | 5 | 5 |
| 0110 | 6 | 6 | 6 |
| 0111 | 7 | 7 | 7 |
| 1000 | 10 | 8 | 8 |
| 1001 | 11 | 9 | 9 |
| 1010 | 12 | 10 | A |
| 1011 | 13 | 11 | B |
| 1100 | 14 | 12 | C |
| 1101 | 15 | 13 | D |
| 1110 | 16 | 14 | E |
| 1111 | 17 | 15 | F |

A "cycle" is defined by completion of one binding reaction and stripping of one or more probes from the substrate. Multiple cycles can be performed on a single substrate or sample. For proteins, multiple cycles will require that the probe removal (stripping) conditions either maintain proteins folded in their proper configuration, or that the probes used are chosen to bind to peptide sequences so that the binding efficiency is independent of the protein fold configuration.

It must be noted that, as used in the specification and the appended claims, the singular forms "a," "an" and "the" include plural referents unless the context clearly dictates otherwise.

OVERVIEW

Compositions and techniques for highly multiplexed single molecule identification and quantification of target analytes using electrical systems are disclosed. In some embodiments the signals are differential signals, generated by comparing the magnitude of two or more signals. Target analytes include protein, peptide, DNA and RNA molecules, with and without modifications. Electrical detection is accomplished using ion sensitive field effect transistors (ISFET) for enhanced sensitivity. Techniques include using tail regions with and without differential stops to identify target analytes. The diversity and sensitivity of the tail regions allow for detailed characterization of target analytes and highly multiplexed target analyte identification. Furthermore, error correction techniques are disclosed that correct potential errors in target analyte detection and characterization.

COMPOSITIONS

A target analyte according to the present invention is any molecule that is to be identified, quantified, and otherwise characterized. A target analyte is usually composed of a protein (denatured or folded), a peptide, or a nucleic acid, but could be another type of molecule such as any small molecule, steroid, or modified nucleic acid comprising an acyl, phosphor, or methyl group. FIG. 1 shows an example of a target analyte 102 that has been immobilized on a substrate. Generally, a target analyte 102 can be at any of a wide range of concentrations (e.g., from the mg/mL to ag/mL range), in any volume of solution (e.g., as low as the picoliter range). For example, samples of blood, serum, formalin-fixed paraffin embedded (FFPE) tissue, saliva, or urine could contain various target analytes 102. The target analytes 102 are recognized by compositions, which are used to identify and quantify the target analytes 102 using electrical detection methods. A composition includes a probe region 104, which is configured to specifically bind to a target analyte 102 of interest. The probe region 104 may be composed of a protein, peptide, or nucleic acid, and is used to recognize and bind to the target analyte 102. In an embodiment, at least a portion of the probe region 104 is composed of an antibody.

Each probe region 104 can be coupled to a tag, or the tail region 106. The tail region 106 is composed of a block of nucleotides of length "N" sufficient to generate by a detector signals that are reliably detected and that can be measured with sufficient accuracy such that the detector can resolve signals arising from blocks of length N, 2N, 3N, 4N, 5N, 6N, 7N, 8N, 9N, 10N, or greater than 10N. In certain embodiments, N can be at least, 10, 15, 25, 50, 100, or greater than 100 nucleotides, and serve as a template for polynucleotide synthesis. The tail region 106 is generally a single-stranded DNA molecule, but could also be an RNA molecule. In one embodiment, the tail region 106 is covalently linked to the probe region 104 through a nucleic acid backbone. In another embodiment, a portion of the tail region 106 specifically binds to a linker region 108, the linker region 108 being covalently linked to the probe region 104 through a nucleic acid backbone. The linker region 108 can be configured to specifically bind to a portion of one tail region, or portions of multiple tail regions. In an embodiment, the linker region 108 is composed of at least 10 nucleotides. In another embodiment, the linker region 108 is composed of 20-25 nucleotides. A probe region 104 may be covalently linked to a single linker region 108, or may be covalently linked to multiple distinct linker regions 108 that each specifically binds to a portion of a distinct tail region 106.

The tail region 106 provides a template for polynucleotide synthesis. During polynucleotide synthesis, one hydrogen ion is released for each nucleotide incorporated along the tail region 106 template. A plurality of these hydrogen ions can be detected as an electrical output signal by a transistor. A minimum threshold number of hydrogen ions must be released for the transistor to detect an electrical output signal. For example, the minimum threshold number can be 25, depending on the configuration of the detector. In that case, the tail region 106 must be at least 25 nucleotides long. In some embodiments, the tail region 106 is at least 25, 100, 200, 1000, or 10,000 nucleotides in length. The tail region 106 often includes one or more homopolymeric base regions. For example, the tail region 106 could be a poly-A, poly-C, poly-G, or a poly-T tail. In an embodiment, the tail region 106 comprises a homopolymeric base region followed by a different homopolymeric base region, for example a poly-A tail followed by a poly-G tail.

The electrical output signal provides information regarding the tail region 106 and its corresponding probe region 104 and target analyte 102. In one example, a sample solution contains multiple target analytes 102. The target analytes 102 are immobilized onto a substrate containing at least one transistor. When a composition configured to specifically bind to one of the target analytes 102 is added, the probe region 104 binds specifically to the target analyte 102. The tail region 106 of this composition is a DNA-based poly-A tail that is 100 nucleotides in length. Thus, when dTTPs are added under conditions that promote polynucleotide synthesis, they will incorporate into the tail region 106, releasing hydrogen ions. If the minimum threshold number of hydrogen ions for the transistor to detect an electrical output signal is 100 nucleotides or less, a transistor will detect an electrical output signal. This signal is used to identify the target analyte 102 associated with the poly-A tail region 106, and potentially determine the concentration of the target analyte 102 in the solution. In one embodiment, the concentration of the target analyte 102 in a sample is determined by counting the number of target analytes immobilized on a substrate, and calibrating by comparisons with a control analyte (for example, a housekeeping gene or known control sequence added during preparation of the sample) of known concentration in the sample, also immobilized on the substrate.

Electrical Detection of Compositions Using Ion-Sensitive Field Effect Transistors The electrical detection methods of the present invention use ion-sensitive field-effect transistors (ISFET, or a pH sensor) to measure hydrogen ion concentrations in solution. In an embodiment, the electrical detection methods disclosed herein are carried out by a computer. The ionic concentration of a solution can be converted to a logarithmic electrical potential by an electrode of an ISFET, and the electrical output signal can be detected and measured. In a further embodiment, the electrical output signal is converted into bits of digital information. ISFETs present a sensitive and specific electrical detection system for the identification and characterization of biomolecules.

For example, ISFETs have previously been used to facilitate DNA sequencing. During the enzymatic conversion of single-stranded DNA into double-stranded DNA, hydrogen ions are released as each nucleotide is added to the DNA molecule. An ISFET detects these released hydrogen ions, thus the ISFET can determine when a nucleotide has been added to the DNA molecule. By synchronizing the incorporation of the nucleoside triphosphates dATP, dCTP, dGTP, and dTTP, the DNA sequence may be determined. For example, if no electrical output signal is detected when the single-stranded DNA template is exposed to dATPs, but an electrical output signal is detected in the presence of dGTPs, the DNA sequence is composed of a complementary cytosine base at the position in question.

In the present invention, an ISFET is used to identify the tail region 106 of a composition, and thus characterize the corresponding target analyte 102. For example, a target analyte 102 may be immobilized on a substrate such as an integrated-circuit chip that contains one or more ISFETs. When the corresponding composition is added and specifically binds to the target analyte 102, and when nucleotides are added that release hydrogen ions when they are incorporated into the tail region 106, the ISFET(s) detects and measures the change in ion concentration. This electrical output signal provides information regarding the identity of the tail region 106.

The simplest type of tail region 106 is one composed entirely of one homopolymeric base region. In this case, there are four possible tail regions 106: a poly-A tail, a poly-C tail, a poly-G tail, and a poly-T tail. However, it is often desirable to have a great diversity in tail regions 106, particularly when detecting hundreds or thousands of target analytes in one sample.

Figure 2A:
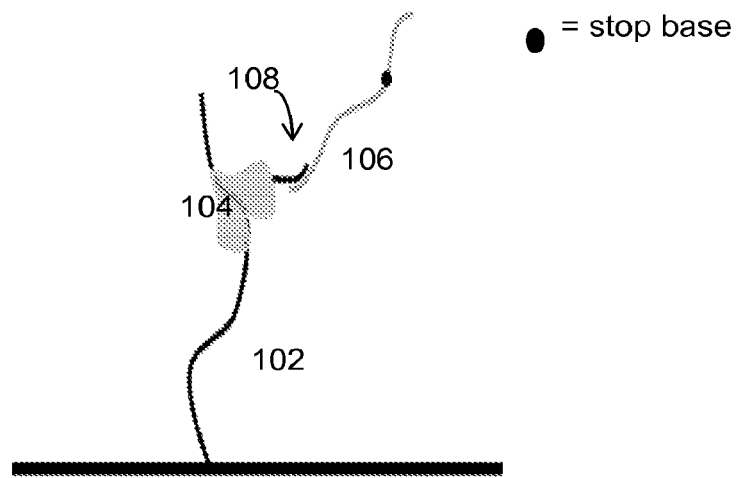
FIGS. 2A and 2B illustrate examples of target analytes immobilized on a substrate and specifically bound to compositions, the compositions including tail regions including one or more stop bases, according to an embodiment.
Figure 2B:
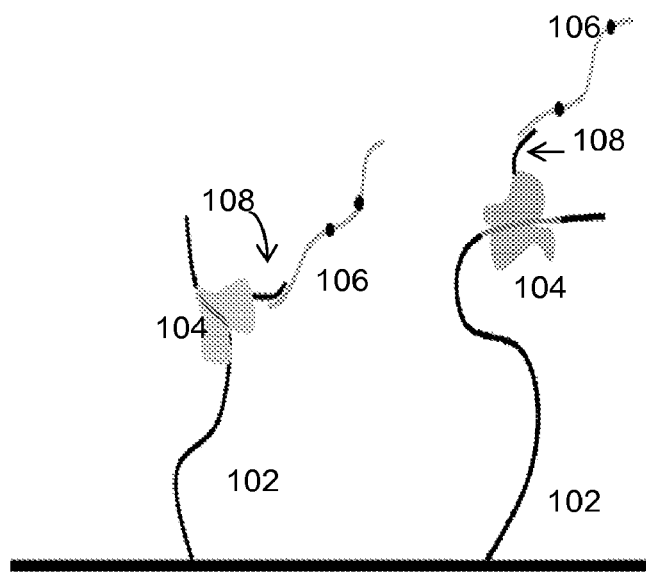

One method of generating diversity in tail regions 106 is by providing one or more stop bases within a homopolymeric base region of a tail region 106. Stop bases are illustrated in FIGS. 2A and 2B. A stop base is a portion of a tail region 106 comprising at least one nucleotide adjacent to a homopolymeric base region, such that the at least one nucleotide is composed of a base that is distinct from the bases within the homopolymeric base region. In one embodiment, the stop base is one nucleotide. In other embodiments, the stop base comprises a plurality of nucleotides. Generally, the stop base is flanked by two homopolymeric base regions. In an embodiment, the two homopolymeric base regions flanking a stop base are composed of the same base. In another embodiment, the two homopolymeric base regions are composed of two different bases. In another embodiment, the tail region 106 contains more than one stop base (FIG. 2B).

In one example, an ISFET can detect a minimum threshold number of 100 hydrogen ions. Target Analyte 1 is bound to a composition with a tail region 106 composed of a 100-nucleotide poly-A tail, followed by one cytosine base, followed by another 100-nucleotide poly-A tail, for a tail region 106 length total of 201 nucleotides. Target Analyte 2 is bound to a composition with a tail region 106 composed of a 200-nucleotide poly-A tail. Upon the addition of dTTPs and under conditions conducive to polynucleotide synthesis, synthesis on the tail region 106 associated with Target Analyte 1 will release 100 hydrogen ions, which can be distinguished from polynucleotide synthesis on the tail region 106 associated with Target Analyte 2, which will release 200 hydrogen ions. The ISFET will detect a distinguishable electrical output signal for each distinct tail region 106. Furthermore, if dGTPs are added, followed by more dTTPs, the tail region 106 associated with Target Analyte 1 will then release one, then 100 more hydrogen ions due to further polynucleotide synthesis. The distinct electrical output signals generated from the addition of specific nucleoside triphosphates based on tail region 106 compositions allow the ISFET to detect and identify specific tail regions 106 and their corresponding target analytes 102.

These electrical detection methods can be used for the simultaneous detection of hundreds (or even thousands) of distinct target analytes. Each target analyte 102 can be associated with a digital identifier, such that the number of distinct digital identifiers is proportional to the number of distinct target analytes in a sample. The identifier may be represented by a number of bits of digital information and is encoded within an ordered tail region 106 set. As discussed further below, each tail region 106 in an ordered tail region 106 set is sequentially made to specifically bind a linker region 108 of a probe region 104 that is specifically bound to the target analyte 102. Alternatively, if the tail regions 106 are covalently bonded to their corresponding probe regions 104, each tail region 106 in an ordered tail region 106 set is sequentially made to specifically bind a target analyte 102.

In one embodiment, one cycle is represented by a binding and stripping of a tail region 106 to a linker region 108, such that polynucleotide synthesis occurs and releases hydrogen ions, which are detected as an electrical output signal. Thus, number of cycles for the identification of a target analyte 102 is equal to the number of tail regions 106 in an ordered tail region 106 set. The number of tail regions 106 in an ordered tail region 106 set is dependent on the number of target analytes to be identified, as well as the total number of bits of information to be generated. In another embodiment, one cycle is represented by a tail region 106 covalently bonded to a probe region 104 specifically binding and being stripped from the target analyte 102.

The electrical output signal detected from each cycle is digitized into bits of information, so that after all cycles have been performed to bind each tail region 106 to its corresponding linker region 108, the total bits of obtained digital information can be used to identify and characterize the target analyte 102 in question. The total number of bits is dependent on a number of identification bits for identification of the target analyte, plus a number of bits for error correction. As explained below, the number of bits for error correction is selected based on the desired robustness and accuracy of the electrical output signal. Generally, the number of error correction bits will be 2 or 3 times the number of identification bits.

In an example, target analytes 102 are immobilized on spatially separate regions of a substrate, which can contain one or more transistors, such as an ISFET. The probe regions 104 are added to the substrate to promote specific binding to the N distinct target analytes 102. One method of characterizing multiple distinct target analytes 102 involves obtaining at least one set of ordered tail regions 106. Each ordered tail region 106 set is composed of one or more tail regions 106, such that each tail region 106 within a set is associated with a probe region 104 that is directed to a distinct target analyte 102 within a defined subset of N distinct target analytes 102. In an embodiment, all of the tail regions 106 have the same nucleotide length. In another embodiment, the number of ordered tail regions 106 in a set is determined based on the number of distinct target analytes 102. In a separate embodiment, the probe regions 104 are covalently linked to the ordered tail regions 106 within a set. In another embodiment, the probe regions 104 contain one or more linker regions 108 and are separate from the set of ordered tail regions 106.

Next, at least M cycles of binding, synthesis, and stripping steps are performed to generate electrical output signals and identify the target analytes 102. A binding is defined by the specific binding of a tail region 106 to a linker region 108 of a probe region 104, or the specific binding of a probe region 104 to a target analyte 102. If the probe regions 104 and tail regions 106 are separate molecules, the cycle begins by adding one ordered set of tail regions 106 corresponding to the probe regions 104 to promote specific binding to the probe regions 104. Then, a synthesis step is performed, during which a reaction mixture of reagents is added under conditions that result in synthesis of a polynucleotide strand using the tail regions 106 as templates. Finally, a stripping step is performed, which includes stripping either the tail regions 106 or the probe regions 104 from the N distinct target analytes 102. In one embodiment, the probe region 104 includes multiple linker regions 108 and is a separate molecule from the tail region 106. Each linker region 108 specifically binds to a portion of a distinct tail region 106. In this case, the stripping step strips only the tail region 106 from a target analyte 102. In another embodiment, the probe region 104 is covalently linked to the tail region 106. In this case, the stripping step strips the entire composition (probe region 104 and tail region 106) from a target analyte 102.

During the synthesis step, an electrical output signal can be detected depending on the release of hydrogen ions during polynucleotide synthesis. From the electrical output signal, at least K bits of information can be obtained per cycle for identification of one or more of the N distinct target analytes 102. Analog-to-digital converters are used to convert the electrical output signal measurements into digital bits of information. This digitizing expands the dynamic range of detection of the signal. In some embodiments, the number of ordered tail regions 106 in a set is determined based on the number of bits of information K obtained per cycle, where $\log_2$ (number of tail regions)=K. The at least K bits of information are used to determine L total bits of information, such that K×M=L bits of information, and L≥$\log_2$(N). The L bits of information are used to identify one or more of the N distinct target analytes 102.

If only one cycle is performed, then only one tail region 106 is used, and K=L. However, more cycles can be performed to generate more bits of information L. If M>1, then multiple cycles are performed, such that a different tail region 106 (in an ordered tail region 106 set, for example) can be associated with a particular target analyte 102 during each cycle. An expected electrical output signal can be associated with a target analyte 102 for each cycle, and compared to the actual electrical output signal. This comparison generates information regarding the accuracy of the identification of the tail region 106 and the associated target analyte 102. A run is represented by a plurality of cycles performed using each of the tail regions 106 in an ordered tail region 106 set to identify one target analyte 102.

In one embodiment, L>$\log_2$(N), such that L includes bits of information that are used for correcting errors in the electrical output signals. While K is equal to the number of bits for identification (of the target analyte) generated per cycle, additional bits for error correction can also be generated per cycle, so that the total number of bits per run L includes both identification bits plus error correction bits. Errors can occur if, for example, a tail region 106 does not properly bind to its corresponding probe region 104 during a cycle. Some of the L bits of information can be used to detect and correct errors by an error correcting code. In one embodiment, the error correcting code is a Reed-Solomon code, which is a nonbinary cyclic code used to detect and correct errors in a system. In addition to the bits of information for target analyte identification, the Reed-Solomon code uses additional bits of information to correct errors. These additional bits are called parity bits, and may be obtained by a variety of well-known techniques, including performing additional cycles. In one embodiment, the number of error correction bits selected is equal to 2 or 3 times the number of identification bits. Other error correcting codes may also be used, for example, block codes, convolution codes, Golay codes, Hamming codes, BCH codes, AN codes, Reed-Muller codes, Goppa codes, Hadamard codes, Walsh codes, Hagelbarger codes, polar codes, repetition codes, repeat-accumulate codes, erasure codes, online codes, group codes, expander codes, constant-weight codes, tornado codes, low-density parity check codes, maximum distance codes, burst error codes, luby transform codes, fountain codes, and raptor codes. See Error Control Coding, 2$^{nd}$ Ed., S. Lin and D J Costello, Prentice Hall, N.Y., 2004.

TABLE 1

Ordered tail region sets for distinct target analytes

| Cycle # | 1 | 2 | 3 | 4 | 5 | 6 | 7 | 8 | Digital identifier |
|---|---|---|---|---|---|---|---|---|---|
| Target 1: L-Selectin | a | b | c | d | e | f | g | h | deabfcgh |
| Target 2: Albumin | i | j | k | l | m | n | o | p | pnmolijk |

Table 1 illustrates examples of ordered tail region sets for target analytes L-selectin and albumin. L-selectin has a digital identifier of "deabfcgh," and the ordered tail region set specific for L-selectin includes 8 distinct tail regions a-h. Here, one distinct tail region is used per cycle. Albumin has a digital identifier of "pnmolijk," and the ordered tail region set specific for albumin includes 8 distinct tail regions i-p. Again, one distinct tail region is used per cycle. For both target analytes, a run is represented by 8 cycles, and the bits of information obtained from the run are used to determine the digital identifier identifying each respective target analyte.

In an embodiment, $L > \log_2(N)$, such that L includes bits of information that are ordered in a predetermined order. For example, if an ordered tail region 106 set predetermines the order of the tail regions to be used per cycle, the bits of information are ordered in a predetermined order. Table 1 shows that for L-selectin, cycle 1 corresponds to tail region "a," and cycle 2 corresponds to tail region "b," for example. In some embodiments, the predetermined order is random. In other embodiments, computer software is used to specify the order. In yet another embodiment, the order of the ordered tail region 106 sets is unknown, and a key is used to decode the order of the ordered tail region 106 sets for each cycle in the at least M cycles. The key may include a number represented by bits, and the bits of the key may be combined with the L bits of information. For example, the ordered tail region 106 set for L-selectin in Table 1 may be scrambled, such that the tail region order for cycles 1-8 is not "abcdefgh," but instead "cdbagfeh." A key may be provided to decode this order to determine the digital identifier for the target analyte in question.

In a further embodiment, another key is used to decode the digital identifier of one or more of the N distinct target analytes 102 depending on the detected electrical output signals for each tail region 106. A key may provide the expected bits of information associated with each tail region 106, or the key may provide the expected bits of information associated with the order of the ordered tail region 106 sets. These expected bits of information provided by the key can be compared with the actual L bits of information determined for a target analyte 102. The comparison can be used to determine the identity of the target analyte 102. For example, the ordered tail regions 106 for L-selectin in Table 1 may not be scrambled, but instead the digital identifier may be scrambled, such that the total number of bits for a run does not identify the digital identifier as "deabfcgh," but as "rstuvwxy." A key may be provided to decode the digital identifier to determine the correct digital identifier for the target analyte in question.

Differential Detection of Single Molecules

Sometimes, several compositions containing distinct tail regions 106 are used to identify and characterize a large number of target analytes 102. In cases like this, differential detection can be used to efficiently identify the tail regions 106. Differential detection uses a plurality of tail regions 106 of the same length that each include homopolymeric base regions composed of the same nucleotide, and include the same number of stop bases. The ratio of the electrical output signals from polynucleotide synthesis between two or more homopolymeric base regions (within one tail region, between stop bases) provides the differential detection measurement. An identification length associated with the tail region 106 is selected, such that the identification length represents a number of nucleotides of the tail region 106 that is required for the release of a particular number of hydrogen ions for detection by a transistor. The longer an identification length, the fewer bits of information are obtained per cycle.

There are various situations in which different identification lengths are desirable. When a longer identification length is used, more hydrogen ions are generated, thus producing more signal for detection. Therefore, the system overall is more accurate. However, a longer identification length results in a longer binding time, fewer bits per cycle, and likely detecting fewer target analytes or requiring a longer time to complete all of the cycles. When a shorter identification length is used, the binding time is shorter, more bits per cycle are obtained, and many target analytes can be detected. However, fewer hydrogen ions are generated, resulting in a less accurate system. In an embodiment, the identification length is equal to a block of nucleotides of length "N" sufficient to generate reliable signals by the detector. In an embodiment, "N" corresponds to the minimum threshold number of hydrogen ions for electrical detection. In another embodiment, the identification length is longer than the minimum threshold number of hydrogen ions for electrical detection. For example, the identification length could be length N, 2N, 3N, 4N, 5N, 6N, 7N, 8N, 9N, 10N, or greater than 10N. In one embodiment, the identification length is equal to the length of the tail region 106. In other embodiments, the identification length is shorter than the length of the tail region 106.

For example, if the identification length is 100 nucleotides, the total tail region 106 length could be 800 nucleotides. This provides 8 discretization lengths. A discretization length is equal to the tail region 106 length divided by the identification length (800/100=8). Each discretization length provides some information regarding the identity of the tail region 106. This information can be digitized as bits of information. The number of bits of information that are generated is equal to the log base 2 of the number of discretization lengths. In this example, there are 8 discretization lengths, or 3 bits of information ($2^3=8$).

When differential detection is used, the stop bases can be in different locations within the different tail regions 106, although the total tail region 106 length should remain constant between all of the tail regions 106. For differential measurements, the length of the tail region 106 is equal to [(number of discretization lengths+1)×(identification length)]+(number of stop bases). Therefore, if there is one stop base in this example, the total tail region 106 length should be (8+1)(100)+1=901 nucleotides. Therefore, the tail regions 106 will be composed of a homopolymeric base region, a stop base, and another homopolymeric base region, such that the homopolymeric base region lengths are based on multiples of the identification length. In this example, assuming the homopolymeric base regions of all of the tail regions 106 are composed of the same base, there can be 8 distinct tail regions 106 with the stop base in a different location for each. On either side of the stop base, the homopolymeric base regions can be 100/800, 200/700, 300/600, 400/500, 500/400, 600/300, 700/200, and 800/100 nucleotides in length. The ratio of the electrical output signal between the two homopolymeric base regions identifies the tail region 106. This signal ratio allows for calibration of the transistor. During electrical detection without differential measurements, the spatial orientation of the target analyte with respect to the transistor can affect the electrical output signal, resulting in inaccurate measurements. However, differential measurements effectively calibrate the system so that such inaccuracies do not occur.

One or more cycles of tail region 106 binding, polynucleotide synthesis, and tail region 106 stripping are performed. As explained above, a different ordered set of tail regions 106 specific for distinct target analytes 102 may be used for each cycle, such that one target analyte 102 may be associated with multiple distinct tail regions 106 during multiple cycles. Each cycle generates a number of bits of information. An optimal system reduces the number and lengths of the tail regions 106 while maximizing the number of bits of information that can be acquired per cycle. Furthermore, it is desirable to minimize the number of cycles, because the stripping of the tail regions 106 may cause damage to the target analytes 102 immobilized on the substrate.

Computer System

Figure 3:
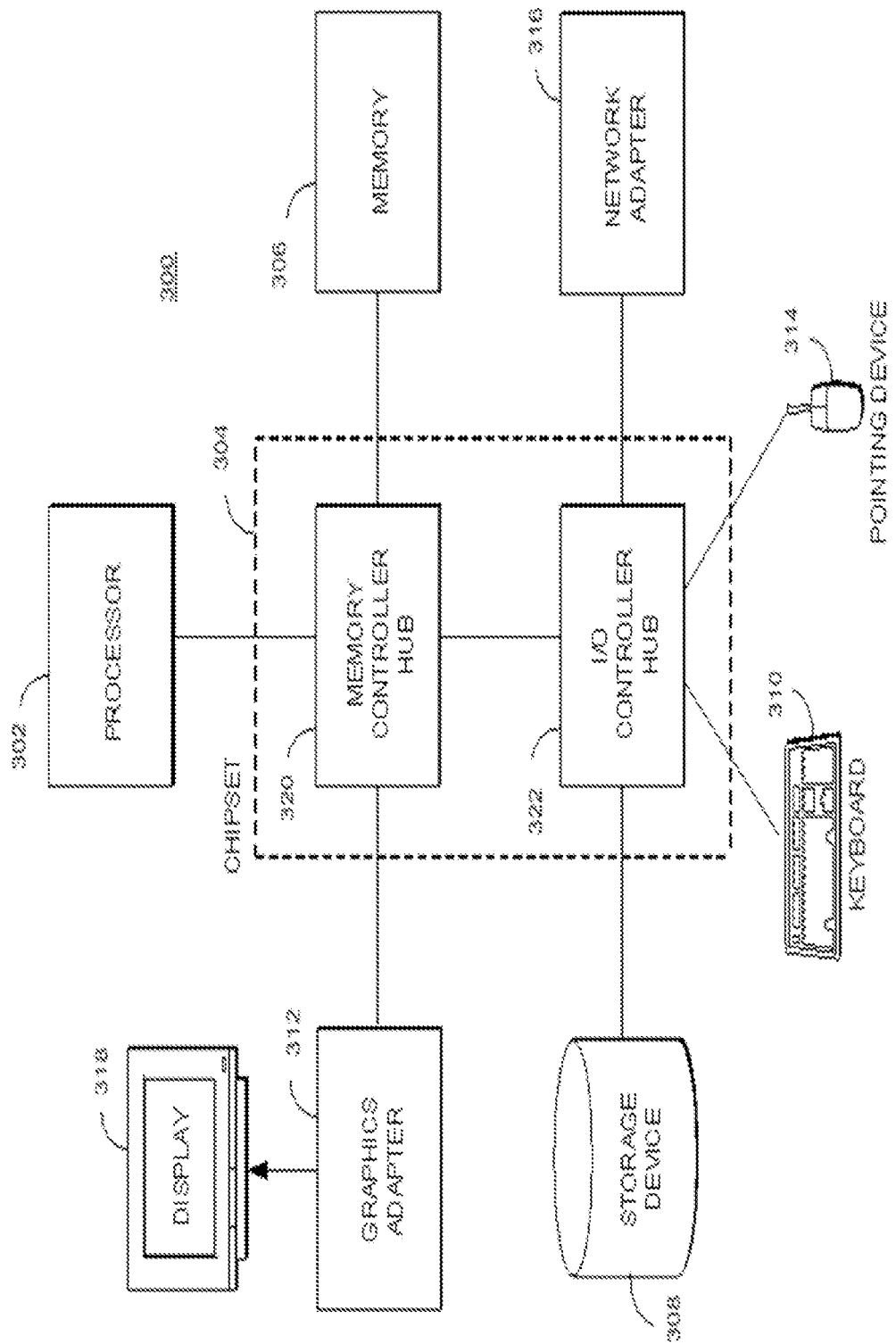
FIG. 3 is a high-level block diagram illustrating an example of a computer 300 for use in analyzing molecular analytes, according to an embodiment.

FIG. 3 is a high-level block diagram illustrating an example of a computer 300 for use in analyzing molecular analytes, in accordance with one embodiment. Illustrated are at least one processor 302 coupled to a chipset 304. The chipset 304 includes a memory controller hub 320 and an input/output (I/O) controller hub 322. A memory 306 and a graphics adapter 312 are coupled to the memory controller hub 322, and a display device 318 is coupled to the graphics adapter 312. A storage device 308, keyboard 310, pointing device 314, and network adapter 316 are coupled to the I/O controller hub 322. Other embodiments of the computer 300 have different architectures. For example, the memory 306 is directly coupled to the processor 302 in some embodiments.

The storage device 308 is a non-transitory computer-readable storage medium such as a hard drive, compact disk read-only memory (CD-ROM), DVD, or a solid-state memory device. The memory 306 holds instructions and data used by the processor 302. The pointing device 314 is used in combination with the keyboard 310 to input data into the computer system 300. The graphics adapter 312 displays images and other information on the display device 318. In some embodiments, the display device 318 includes a touch screen capability for receiving user input and selections. The network adapter 316 couples the computer system 300 to the network. Some embodiments of the computer 300 have different and/or other components than those shown in FIG. 3. For example, the server can be formed of multiple blade servers and lack a display device, keyboard, and other components.

The computer 300 is adapted to execute computer program modules for providing functionality described herein. As used herein, the term "module" refers to computer program instructions and other logic used to provide the specified functionality. Thus, a module can be implemented in hardware, firmware, and/or software. In one embodiment, program modules formed of executable computer program instructions are stored on the storage device 308, loaded into the memory 306, and executed by the processor 302.

EXAMPLES

The following Examples illustrate target analyte identification experiments using differential detection techniques.

Example 1

There are 8 distinct target analytes 102 immobilized on an integrated-circuit chip containing a plurality of transistors (i.e., ISFETs). Each target analyte 102 is specific for a distinct probe region 104 that includes one or more linker regions 108, each of which is specific for a particular tail region 106. 8 poly-A tail regions 106 are used in this Example, all having a length of 901 nucleotides. The identification length is 100 nucleotides, and one stop base of one stop base type (cytosine) is inserted within the tail. Table 1A shows the different tail regions 106 used, where "Leader length" represents the number of nucleotides upstream of the stop base, and "Trailer length" represents the number of nucleotides downstream of the stop base.

TABLE 1A

| Tail region Number | Leader length | Stop Base | Trailer length |
|---|---|---|---|
| Tail region #1 | 100 | C | 800 |
| Tail region #2 | 200 | C | 700 |
| Tail region #3 | 300 | C | 600 |
| Tail region #4 | 400 | C | 500 |
| Tail region #5 | 500 | C | 400 |
| Tail region #6 | 600 | C | 300 |
| Tail region #7 | 700 | C | 200 |
| Tail region #8 | 800 | C | 100 |

The number of bits for identification of a target analyte 102 is equal to $\log_2(N)$, such that N=number of distinct target analytes 102. In this case, $\log_2(8)=3$ bits for identification. 9 bits of error correction are selected. Thus, the total number of bits per run (a run represents all of the cycles) is 12 (3+9=12). 3 bits of information are selected to be generated per cycle, such that $\log_2$ (number of tail regions) =number of bits/cycle, so $\log_2(8)=3$. Therefore, this scheme requires 4 cycles of binding and stripping (12 total bits divided by 3 bits per cycle=4 cycles). Furthermore, there will be 3 flow sequences per cycle. There are one or more sequential flow sequences per cycle, such that each flow sequence is the addition of a different type of base (a "flow base") that allows polynucleotide synthesis to occur. For example, because the tail region 106 is a poly-A tail with one cytosine stop base, dTTPs must first be added to begin polynucleotide synthesis on the poly-A tail. This is one flow sequence. Next, dGTPs must be added to incorporate into the cytosine stop base (the second flow sequence), and then dTTPs are again added to finish polynucleotide synthesis (the third flow sequence). Table 1B below illustrates the flow sequences, showing that each cycle consists of 3 flow sequences.

TABLE 1B

| Flow Sequence Number | Flow Base | Description |
| --- | --- | --- |
| Sequence #1 | T | Trailer length ID |
| Sequence #2 | G | Remove stop base 'C' |
| Sequence #3 | T | Leader length ID |

At the end of the run, 3 bits of information for identification of a target analyte 102 are generated, and 9 bits of error correction providing information regarding the accuracy of the identification are generated. These bits of information identify and characterize the tail regions 106 and their associated target analytes 102.

Example 2

There are 16 distinct target analytes 102 immobilized on an integrated-circuit chip containing a plurality of transistors. Each target analyte 102 is specific for a distinct probe region 104 that includes one or more linker regions 108, each of which is specific for a particular tail region 106. 16 poly-A tail regions 106 are used in this Example, all having a length of 701 nucleotides. The identification length is 100, and one stop base of three stop base types (cytosine, guanine, or thymine) is inserted within the tail. Table 2A shows the different tail regions 106 used, where "Leader length" represents the number of nucleotides upstream of the stop base, and "Trailer length" represents the number of nucleotides downstream of the stop base.

TABLE 2A

| Tail region Number | Leader length | Stop Base | Trailer length |
| --- | --- | --- | --- |
| Tail region #1 | 100 | C | 600 |
| Tail region #2 | 200 | C | 500 |
| Tail region #3 | 300 | C | 400 |
| Tail region #4 | 400 | C | 300 |
| Tail region #5 | 500 | C | 200 |
| Tail region #6 | 600 | C | 100 |
| Tail region #7 | 100 | G | 600 |
| Tail region #8 | 200 | G | 500 |
| Tail region #9 | 300 | G | 400 |
| Tail region #10 | 400 | G | 300 |
| Tail region #11 | 500 | G | 200 |
| Tail region #12 | 600 | G | 100 |
| Tail region #13 | 100 | T | 600 |
| Tail region #14 | 200 | T | 500 |
| Tail region #15 | 300 | T | 400 |
| Tail region #16 | 400 | T | 300 |

The number of bits for identification of a target analyte 102 is equal to $\log_2(N)$, such that N=number of distinct target analytes 102. In this case, $\log_2(16)=4$ bits for identification. 12 bits of error correction are selected to provide information regarding the accuracy of the identification. Thus, the total number of bits per run is 16 (4+12=16). 4 bits of information are selected to be generated per cycle, such that $\log_2$ (number of tail regions)=number of bits/cycle, so $\log_2(16)=4$. Therefore, this scheme requires 4 cycles of binding and stripping (16 total bits divided by 4 bits per cycle=4 cycles). Furthermore, there will be 7 flow sequences per cycle, as illustrated in Table 2B below.

TABLE 2B

| Flow Sequence Number | Flow Nucleotide | Description |
| --- | --- | --- |
| Sequence #1 | T | Trailer length ID |
| Sequence #2 | G | Remove stop base 'C' |
| Sequence #3 | T | Leader length ID |
| Sequence #4 | C | Remove stop base 'G' |
| Sequence #5 | T | Leader length ID |
| Sequence #6 | A | Remove stop base, 'T' |
| Sequence #7 | T | Leader length ID |

At the end of the run, 4 bits of information for identification of a target analyte 102 are generated, and 12 bits of error correction providing information regarding the accuracy of the identification are generated. These bits of information identify and characterize the tail regions 106 and their associated target analytes 102.

Example 3

There are 256 distinct target analytes 102 immobilized on an integrated-circuit chip containing a plurality of transistors. Each target analyte 102 is specific for a distinct probe region 104 that includes one or more linker regions 108, each of which is specific for a particular tail region 106. 16 poly-A tail regions 106 are used in this Example, all having a length of 402 nucleotides. The identification length is 100, and two stop bases of a combination of three stop base types (cytosine, guanine, or thymine) are inserted within the tail. Table 3A shows the different tail regions 106 used, where "Leader length" represents the number of nucleotides upstream of Stop base #1, "Mid length" represents the number of nucleotides upstream of Stop base #2, and "Trailer length" represents the number of nucleotides downstream of Stop base #2.

TABLE 3A

| Tail region 106 number | Leader length | Stop base #1 | Mid Length | Stop base #2 | Trailer length |
| --- | --- | --- | --- | --- | --- |
| Tail region #1 | 100 | C | 100 | C | 200 |
| Tail region #2 | 100 | C | 200 | C | 100 |
| Tail region #3 | 200 | C | 100 | C | 100 |
| Tail region #4 | 100 | C | 100 | G | 200 |
| Tail region #5 | 100 | C | 200 | G | 100 |
| Tail region #6 | 200 | C | 100 | G | 100 |
| Tail region #7 | 100 | C | 100 | T | 200 |
| Tail region #8 | 100 | C | 200 | T | 100 |
| Tail region #9 | 200 | C | 100 | T | 100 |
| Tail region #10 | 100 | G | 100 | C | 200 |
| Tail region #11 | 100 | G | 200 | C | 100 |
| Tail region #12 | 200 | G | 100 | C | 100 |
| Tail region #13 | 100 | G | 100 | G | 200 |
| Tail region #14 | 100 | G | 200 | G | 100 |
| Tail region #15 | 200 | G | 100 | G | 100 |
| Tail region #16 | 100 | G | 100 | T | 200 |

The number of bits for identification of a target analyte 102 is equal to $\log_2(N)$, such that N=number of distinct target analytes 102. In this case, $\log_2(256)=8$ bits for identification. 24 bits of error correction are selected to provide information regarding the accuracy of the identification. Thus, the total number of bits per run is 32 (8+24=32). 4 bits of information are selected to be generated per cycle, such that $\log_2$ (number of tail regions)=number of bits/cycle, so $\log_2(16)=4$. Therefore, this scheme requires 8 cycles of binding and stripping (32 total bits divided by 4 bits per cycle=8 cycles). Furthermore, there will be 13 flow sequences per cycle, as illustrated in Table 3B below.

TABLE 3B

| Flow Sequence Number | Flow Nucleotide | Description |
|---|---|---|
| Sequence #1 | T | Trailer length ID |
| Sequence #2 | G | Remove stop 2 base 'C' |
| Sequence #3 | T | Mid length ID |
| Sequence #4 | C | Remove stop 2 base 'G' |
| Sequence #5 | T | Mid length ID |
| Sequence #6 | A | Remove stop 2 base, 'T' |
| Sequence #7 | T | Mid length ID |
| Sequence #8 | G | Remove stop 1 base 'C' |
| Sequence #9 | T | Leader length ID |
| Sequence #10 | C | Remove stop 1 base 'G' |
| Sequence #11 | T | Leader length ID |
| Sequence #12 | A | Remove stop 1 base, 'T' |
| Sequence #13 | T | Leader length ID |

At the end of the run, 8 bits of information for identification of a target analyte 102 are generated, and 24 bits of error correction providing information regarding the accuracy of the identification are generated. These bits of information identify and characterize the tail regions 106 and their associated target analytes 102.

Example 4

There are 4,096 distinct target analytes 102 immobilized on an integrated-circuit chip containing a plurality of transistors. Each target analyte 102 is specific for a distinct probe region 104 that includes one or more linker regions 108, each of which is specific for a particular tail region 106. 64 poly-A tail regions 106 (84 poly-A tail regions 106 are shown in Table 4A, but only 64 are used) are used in this Example, all having a length of 802 nucleotides. The identification length is 100, and two stop bases of a combination of two stop base types (cytosine or guanine) are inserted within the tail. Table 4A shows the different tail regions 106 used, where "Leader" represents the number of nucleotides (×100) upstream of stop base #1, "Mid" represents the number of nucleotides (×100) upstream of stop base #2, and "Trailer" represents the number of nucleotides (×100) downstream of stop base #2.

TABLE 4A

| Index | Levels | Leader | Stop 1 | Mid | Stop 2 | Trailer |
|---|---|---|---|---|---|---|
| 1 | 8 | 1 | C | 1 | C | 6 |
| 2 | 8 | 1 | C | 2 | C | 5 |
| 3 | 8 | 1 | C | 3 | C | 4 |
| 4 | 8 | 1 | C | 4 | C | 3 |
| 5 | 8 | 1 | C | 5 | C | 2 |
| 6 | 8 | 1 | C | 6 | C | 1 |
| 7 | 8 | 2 | C | 1 | C | 5 |
| 8 | 8 | 2 | C | 2 | C | 4 |
| 9 | 8 | 2 | C | 3 | C | 3 |
| 10 | 8 | 2 | C | 4 | C | 2 |
| 11 | 8 | 2 | C | 5 | C | 1 |
| 12 | 8 | 3 | C | 1 | C | 4 |
| 13 | 8 | 3 | C | 2 | C | 3 |
| 14 | 8 | 3 | C | 3 | C | 2 |
| 15 | 8 | 3 | C | 4 | C | 1 |
| 16 | 8 | 4 | C | 1 | C | 3 |
| 17 | 8 | 4 | C | 2 | C | 2 |
| 18 | 8 | 4 | C | 3 | C | 1 |
| 19 | 8 | 5 | C | 1 | C | 2 |
| 20 | 8 | 5 | C | 2 | C | 1 |
| 21 | 8 | 6 | C | 1 | C | 1 |
| 22 | 8 | 1 | C | 1 | G | 6 |
| 23 | 8 | 1 | C | 2 | G | 5 |
| 24 | 8 | 1 | C | 3 | G | 4 |
| 25 | 8 | 1 | C | 4 | G | 3 |
| 26 | 8 | 1 | C | 5 | G | 2 |
| 27 | 8 | 1 | C | 6 | G | 1 |
| 28 | 8 | 2 | C | 1 | G | 5 |
| 29 | 8 | 2 | C | 2 | G | 4 |
| 30 | 8 | 2 | C | 3 | G | 3 |
| 31 | 8 | 2 | C | 4 | G | 2 |
| 32 | 8 | 2 | C | 5 | G | 1 |
| 33 | 8 | 3 | C | 1 | G | 4 |
| 34 | 8 | 3 | C | 2 | G | 3 |
| 35 | 8 | 3 | C | 3 | G | 2 |
| 36 | 8 | 3 | C | 4 | G | 1 |
| 37 | 8 | 4 | C | 1 | G | 3 |
| 38 | 8 | 4 | C | 2 | G | 2 |
| 39 | 8 | 4 | C | 3 | G | 1 |
| 40 | 8 | 5 | C | 1 | G | 2 |
| 41 | 8 | 5 | C | 2 | G | 1 |
| 42 | 8 | 6 | C | 1 | G | 1 |
| 43 | 8 | 1 | G | 1 | C | 6 |
| 44 | 8 | 1 | G | 2 | C | 5 |
| 45 | 8 | 1 | G | 3 | C | 4 |
| 46 | 8 | 1 | G | 4 | C | 3 |
| 47 | 8 | 1 | G | 5 | C | 2 |
| 48 | 8 | 1 | G | 6 | C | 1 |
| 49 | 8 | 2 | G | 1 | C | 5 |
| 50 | 8 | 2 | G | 2 | C | 4 |
| 51 | 8 | 2 | G | 3 | C | 3 |
| 52 | 8 | 2 | G | 4 | C | 2 |
| 53 | 8 | 2 | G | 5 | C | 1 |
| 54 | 8 | 3 | G | 1 | C | 4 |
| 55 | 8 | 3 | G | 2 | C | 3 |
| 56 | 8 | 3 | G | 3 | C | 2 |
| 57 | 8 | 3 | G | 4 | C | 1 |
| 58 | 8 | 4 | G | 1 | C | 3 |
| 59 | 8 | 4 | G | 2 | C | 2 |
| 60 | 8 | 4 | G | 3 | C | 1 |
| 61 | 8 | 5 | G | 1 | C | 2 |
| 62 | 8 | 5 | G | 2 | C | 1 |
| 63 | 8 | 6 | G | 1 | C | 1 |
| 64 | 8 | 1 | G | 1 | G | 6 |
| 65 | 8 | 1 | G | 2 | G | 5 |
| 66 | 8 | 1 | G | 3 | G | 4 |
| 67 | 8 | 1 | G | 4 | G | 3 |
| 68 | 8 | 1 | G | 5 | G | 2 |
| 69 | 8 | 1 | G | 6 | G | 1 |
| 70 | 8 | 2 | G | 1 | G | 5 |
| 71 | 8 | 2 | G | 2 | G | 4 |
| 72 | 8 | 2 | G | 3 | G | 3 |
| 73 | 8 | 2 | G | 4 | G | 2 |
| 74 | 8 | 2 | G | 5 | G | 1 |
| 75 | 8 | 3 | G | 1 | G | 4 |
| 76 | 8 | 3 | G | 2 | G | 3 |
| 77 | 8 | 3 | G | 3 | G | 2 |
| 78 | 8 | 3 | G | 4 | G | 1 |
| 79 | 8 | 4 | G | 1 | G | 3 |
| 80 | 8 | 4 | G | 2 | G | 2 |
| 81 | 8 | 4 | G | 3 | G | 1 |
| 82 | 8 | 5 | G | 1 | G | 2 |
| 83 | 8 | 5 | G | 2 | G | 1 |
| 84 | 8 | 6 | G | 1 | G | 1 |

The number of bits for identification of a target analyte 102 is equal to $\log_2(N)$, such that N=number of distinct target analytes 102. In this case, $\log_2(4,096)=12$ bits for identification. 36 bits of error correction are selected to provide information regarding the accuracy of the identification. Thus, the total number of bits per run is 48 (12+36=48). 6 bits of information are selected to be generated per cycle, such that $\log_2$ (number of tail regions)=number of bits/cycle, so $\log_2(64)=6$. Therefore, this scheme requires 6 cycles of binding and stripping (48 total bits divided by 6 bits per cycle=8 cycles). Furthermore, there will be 9 flow sequences per cycle, as illustrated in Table 4B below.

TABLE 4B

| Flow Sequence Number | Flow Nucleotide | Description |
|---|---|---|
| Sequence #1 | T | Trailer length ID, all tags |
| Sequence #2 | G | Remove stop 2 base 'C' |
| Sequence #3 | T | Mid length ID, 'C' |
| Sequence #4 | C | Remove stop 2 base 'G' |
| Sequence #5 | T | Mid length ID, 'G' |
| Sequence #6 | G | Remove stop 1 base 'C' |
| Sequence #7 | T | Leader length ID, 'C' |
| Sequence #8 | C | Remove stop 1 base 'G' |
| Sequence #9 | T | Leader length ID, 'G' |

At the end of the run, 12 bits of information for identification of a target analyte 102 are generated, and 36 bits of error correction providing information regarding the accuracy of the identification are generated. These bits of information identify and characterize the tail regions 106 and their associated target analytes 102.

Example 5

There are 65,536 distinct target analytes 102 immobilized on an integrated-circuit chip containing a plurality of transistors. Each target analyte 102 is specific for a distinct probe region 104 that includes one or more linker regions 108, each of which is specific for a particular tail region 106. 256 poly-A tail regions 106 (324 poly-A tail regions 106 are shown in Table 5A, but only 256 are used) are used in this Example, all having a length of 1002 nucleotides. The identification length is 100, and two stop bases of a combination of three stop base types (cytosine, guanine, or thymine) are inserted within the tail. Table 5A shows the different tail regions 106 used, where, for example, 1C1C8 represents a tail region 106 consisting of 1×100 poly-A nucleotides, one cytosine stop base, 1×100 poly-A nucleotides, a second cytosine stop base, and 8×100 poly-A nucleotides.

TABLE 5A

| | | | | | | | |
|---|---|---|---|---|---|---|---|
| 1C1C8 | 1C2C7 | 1C3C6 | 1C4C5 | 1C5C4 | 1C6C3 | 1C7C2 | 1C8C1 |
| 2C1C7 | 2C2C6 | 2C3C5 | 2C4C4 | 2C5C3 | 2C6C2 | 2C7C1 | 3C1C6 |
| 3C2C5 | 3C3C4 | 3C4C3 | 3C5C2 | 3C6C1 | 4C1C5 | 4C2C4 | 4C3C3 |
| 4C4C2 | 4C5C1 | 5C1C4 | 5C2C3 | 5C3C2 | 5C4C1 | 6C1C3 | 6C2C1 |
| 6C3C1 | 7C1C2 | 7C2C1 | 8C1G1 | 1C1G8 | 1C2G7 | 1C3G6 | 1C4G5 |
| 1C5G4 | 1C6G3 | 1C7G2 | 1C8G1 | 2C1G7 | 2C2G6 | 2C3G5 | 2C4G4 |
| 2C5G3 | 2C6G2 | 2C7G1 | 3C1G6 | 3C2G5 | 3C3G4 | 3C4G3 | 3C5G2 |
| 3C6G1 | 4C1G5 | 4C2G4 | 4C3G3 | 4C4G2 | 4C5G1 | 5C1G4 | 5C2G3 |
| 5C3G2 | 5C4G1 | 6C1G3 | 6C2G2 | 6C3G1 | 7C1G2 | 7C2G1 | 8C1G1 |
| 1C1T8 | 1C2T7 | 1C3T6 | 1C4T5 | 1C5T4 | 1C6T3 | 1C7T2 | 1C8T1 |
| 2C1T7 | 2C2T6 | 2C3T5 | 2C4T4 | 2C5T3 | 2C6T2 | 2C7T1 | 3C1T6 |
| 3C2T5 | 3C3T4 | 3C4T3 | 3C5T2 | 3C6T1 | 4C1T5 | 4C2T4 | 4C3T3 |
| 4C4T2 | 4C5T1 | 5C1T4 | 5C2T3 | 5C3T2 | 5C4T1 | 6C1T3 | 6C2T2 |
| 6C3T1 | 7C1T2 | 7C2T1 | 8C1T1 | 1G1C8 | 1G2C7 | 1G3C6 | 1G4C5 |
| 1G5C4 | 1G6C3 | 1G7C2 | 1G8C1 | 2G1C7 | 2G2C6 | 2G3C5 | 2G4C4 |
| 2G5C3 | 2G6C2 | 2G7C1 | 3G1C6 | 3G2C5 | 3G3C4 | 3G4C3 | 3G5C2 |
| 3G6C1 | 4G1C5 | 4G2C4 | 4G3C3 | 4G4C2 | 4G5C1 | 5G1C4 | 5G2C3 |
| 5G3C2 | 5G4C1 | 6G1C3 | 6G2C2 | 6G3C1 | 7G1C2 | 7G2C1 | 8G1G1 |
| 1G1G8 | 1G2G7 | 1G3G6 | 1G4G5 | 1G5G4 | 1G6G3 | 1G7G2 | 1G8G1 |
| 2G1G7 | 2G2G6 | 2G3G5 | 2G4G4 | 2G5G3 | 2G6G2 | 2G7G1 | 3G1G6 |
| 3G2G5 | 3G3G4 | 3G4G3 | 3G5G2 | 3G6G1 | 4G1G5 | 4G2G4 | 4G3G3 |
| 4G4G2 | 4G5G1 | 5G1G4 | 5G2G3 | 5G3G2 | 5G4G1 | 6G1G3 | 6G2G2 |
| 6G3G1 | 7G1G2 | 7G2G1 | 8G1G1 | 1G1T8 | 1G2T7 | 1G3T6 | 1G4T5 |
| 1G5T4 | 1G6T3 | 1G7T2 | 1G8T1 | 2G1T7 | 2G2T6 | 2G3T5 | 2G4T4 |
| 2G5T3 | 2G6T2 | 2G7T1 | 3G1T6 | 3G2T5 | 3G3T4 | 3G4T3 | 3G5T2 |
| 3G6T1 | 4G1T5 | 4G2T4 | 4G3T3 | 4G4T2 | 4G5T1 | 5G1T4 | 5G2T3 |
| 5G3T2 | 5G4T1 | 6G1T3 | 6G2T2 | 6G3T1 | 7G1T2 | 7G2T1 | 8G1T1 |
| 1T1C8 | 1T2C7 | 1T3C6 | 1T4C5 | 1T5C4 | 1T6C3 | 1T7C2 | 1T8C1 |
| 2T1C7 | 2T2C6 | 2T3C5 | 2T4C4 | 2T5C3 | 2T6C2 | 2T7C1 | 3T1C6 |
| 3T2C5 | 3T3C4 | 3T4C3 | 3T5C2 | 3T6C1 | 4T1C5 | 4T2C4 | 4T3C3 |
| 4T4C2 | 4T5C1 | 5T1C4 | 5T2C3 | 5T3C2 | 5T4C1 | 6T1C3 | 6T2C2 |
| 6T3C1 | 7T1C2 | 7T2C1 | 8T1G1 | 1T1G8 | 1T2G7 | 1T3G6 | 1T4G5 |
| 1T5G4 | 1T6G3 | 1T7G2 | 1T8G1 | 2T1G7 | 2T2G6 | 2T3G4 | 2T4G4 |
| 2T5G3 | 2T6G2 | 2T7G1 | 3T1G6 | 3T2G5 | 3T3G4 | 3T4G3 | 3T5G2 |
| 3T6G1 | 4T1G5 | 4T2G4 | 4T3G3 | 4T4G2 | 4T5G1 | 5T1G4 | 5T2G3 |
| 5T3G2 | 5T4G1 | 6T1G3 | 6T2G2 | 6T3G1 | 7T1G2 | 7T2G1 | 8T1G1 |
| 1T1T8 | 1T2T7 | 1T3T6 | 1T4T5 | 1T5T4 | 1T6T3 | 1T7T2 | 1T8T1 |
| 2T1T7 | 2T2T6 | 2T3T5 | 2T4T4 | 2T5T3 | 2T6T2 | 2T7T1 | 3T1T6 |
| 3T2T5 | 3T3T4 | 3T4T3 | 3T5T2 | 3T6T1 | 4T1T5 | 4T2T4 | 4T3T3 |
| 4T4T2 | 4T5T1 | 5T1T4 | 5T2T3 | 5T3T2 | 5T4T1 | 6T1T3 | 6T2T2 |
| 6T3T1 | 7T1T2 | 7T2T1 | 8T1T1 | | | | |

The number of bits for identification of a target analyte 102 is equal to $\log_2(N)$, such that N=number of distinct target analytes 102. In this case, $\log_2(65,536)=16$ bits for identification. 48 bits of error correction are selected to provide information regarding the accuracy of the identification. Thus, the total number of bits per run is 64 (16+48=64). 8 bits of information are selected to be generated per cycle, such that $\log_2$ (number of tail regions)=number of bits/cycle, so $\log_2(256)=8$. Therefore, this scheme requires 8 cycles of binding and stripping (64 total bits divided by 8 bits per cycle=8 cycles). Furthermore, there will be 13 flow sequences per cycle, as illustrated in Table 4B below.

TABLE 5B

| Flow Sequence Number | Flow Nucleotide | Description |
|---|---|---|
| Sequence #1 | T | Trailer length ID, all tags |
| Sequence #2 | G | Remove stop 2 base 'C' |
| Sequence #3 | T | Mid length ID, 'C' |
| Sequence #4 | C | Remove stop 2 base 'G' |
| Sequence #5 | T | Mid length ID, 'G' |
| Sequence #6 | A | Remove stop 2 base, 'T' |
| Sequence #7 | T | Mid length ID, 'T' |
| Sequence #8 | G | Remove stop 1 base 'C' |
| Sequence #9 | T | Leader length ID, 'C' |
| Sequence #10 | C | Remove stop 1 base 'G' |
| Sequence #11 | T | Leader length ID, 'G' |
| Sequence #12 | A | Remove stop 1 base, 'T' |
| Sequence #13 | T | Leader length ID, 'T' |

At the end of the run, 16 bits of information for identification of a target analyte 102 are generated, and 48 bits of error correction providing information regarding the accuracy of the identification are generated. These bits of information identify and characterize the tail regions 106 and their associated target analytes 102.

In other examples, even more distinct target analytes 102 can be analyzed on one chip, and various numbers of bits can be selected to be generated per cycle. Table 6A illustrates a number of required bits per run for varying numbers of simultaneous targets. Table 6B shows various numbers of cycles determined from the total number of bits per run.

TABLE 6A

Varying Numbers of Possible Simultaneous Targets

| # ID's (# of possible simultaneous targets) | # Bits of ID | # Bits of Error Correction (bits$_{ID}$ × 1) | # Bits of Error Correction (bits$_{ID}$ × 2) | # Bits of Error Correction (bits$_{ID}$ × 3) | Total # of Bits per Run (bits$_{ID}$ × 1) | Total # of Bits per Run (bits$_{ID}$ × 2) | Total # of Bits per Run (bits$_{ID}$ × 3) |
|---|---|---|---|---|---|---|---|
| 4 | 2 | 2 | 4 | 6 | 4 | 6 | 8 |
| 8 | 3 | 3 | 6 | 9 | 6 | 9 | 12 |
| | | | | | | | Ex #1 |
| 16 | 4 | 4 | 8 | 12 | 8 | 12 | 16 |
| | | | | | | | Ex #2 |
| 32 | 5 | 5 | 10 | 15 | 10 | 15 | 20 |
| 64 | 6 | 6 | 12 | 18 | 12 | 18 | 24 |
| 128 | 7 | 7 | 14 | 21 | 14 | 21 | 28 |
| 256 | 8 | 8 | 16 | 24 | 16 | 24 | 32 |
| | | | | | | | Ex #3 |
| 512 | 9 | 9 | 18 | 27 | 18 | 27 | 36 |
| 1,024 | 10 | 10 | 20 | 30 | 20 | 30 | 40 |
| 2,048 | 11 | 11 | 22 | 33 | 22 | 33 | 44 |
| 4,096 | 12 | 12 | 24 | 36 | 24 | 36 | 48 |
| | | | | | | | Ex #4 |
| 8,192 | 13 | 13 | 26 | 29 | 26 | 29 | 52 |
| 16,384 | 14 | 14 | 28 | 42 | 28 | 42 | 56 |
| 32,768 | 15 | 15 | 30 | 45 | 30 | 45 | 60 |
| 65,536 | 16 | 16 | 32 | 48 | 32 | 48 | 64 |
| | | | | | | | Ex #5 |
| 131,072 | 17 | 17 | 34 | 51 | 34 | 51 | 68 |
| 262,144 | 18 | 18 | 36 | 54 | 36 | 54 | 72 |

TABLE 6B

Number of Cycles from Bits per Run

| Total # of Bits per Run | # Cycles 1 bit per cycle) | # Cycles 2 bits per cycle) | # Cycles 3 bits per cycle) | # Cycles 4 bits per cycle) | # Cycles 5 bits per cycle) | # Cycles 6 bits per cycle) | # Cycles 7 bits per cycle) | # Cycles 8 bits per cycle) |
|---|---|---|---|---|---|---|---|---|
| 4 | 4 | 2 | 2 | 1 | 1 | 1 | 1 | 1 |
| 8 | 8 | 4 | 3 | 2 | 2 | 2 | 2 | 1 |
| 12 | 12 | 6 | 4 | 3 | 3 | 2 | 2 | 2 |
| 16 | 16 | 8 | 6 | 4 | 4 | 3 | 3 | 2 |
| | | | Ex #1 | | | | | |
| 20 | 30 | 10 | 7 | 5 | 4 | 4 | 3 | 3 |
| 24 | 24 | 12 | 8 | 6 | 5 | 4 | 4 | 3 |
| | | | | Ex #2 | | | | |
| 28 | 28 | 14 | 10 | 7 | 6 | 5 | 4 | 4 |
| 32 | 32 | 16 | 11 | 8 | 7 | 6 | 5 | 4 |
| | | | | Ex #3 | | | | |
| 36 | 36 | 18 | 12 | 9 | 8 | 6 | 6 | 5 |
| 40 | 40 | 20 | 14 | 10 | 8 | 7 | 6 | 5 |
| 44 | 44 | 22 | 15 | 11 | 9 | 8 | 7 | 6 |
| 48 | 48 | 24 | 16 | 12 | 10 | 8 | 7 | 6 |
| | | | | | Ex #4 | | | |
| 52 | 52 | 26 | 18 | 13 | 11 | 9 | 8 | 7 |
| 56 | 56 | 28 | 19 | 14 | 12 | 10 | 8 | 7 |
| 60 | 60 | 30 | 20 | 15 | 12 | 10 | 9 | 8 |
| 64 | 64 | 32 | 22 | 16 | 13 | 11 | 10 | 8 |
| | | | | | | | | Ex #5 |
| 68 | 68 | 34 | 23 | 17 | 14 | 12 | 10 | 9 |
| 72 | 72 | 36 | 24 | 18 | 15 | 12 | 11 | 9 |

Furthermore, a number of bits obtained per cycle could change based on the number of stop bases used. Table 7A shows the number of bits per cycle when one stop base is used, and Table 7B shows the number of bits per cycle when two stop bases are used.

TABLE 7A

Bits Per Cycle, One Stop Base

| # Levels | # Stops | # Stop Types | # Probes | # Bits Per Cycle |
|---|---|---|---|---|
| 3 | 1 | 1 | 2 | 1.00 |
| 4 | 1 | 1 | 3 | 1.58 |
| 5 | 1 | 1 | 4 | 2.00 |
| 6 | 1 | 1 | 5 | 2.32 |
| 7 | 1 | 1 | 6 | 2.58 |
| 8 | 1 | 1 | 7 | 2.81 |
| 9 | 1 | 1 | 8 | 3.00 Ex #1 |
| 10 | 1 | 1 | 9 | 3.17 |
| 3 | 1 | 2 | 4 | 2.00 |
| 4 | 1 | 2 | 6 | 2.58 |
| 5 | 1 | 2 | 8 | 3.00 |
| 6 | 1 | 2 | 10 | 3.32 |
| 7 | 1 | 2 | 12 | 3.58 |
| 8 | 1 | 2 | 14 | 3.81 |
| 9 | 3 | 2 | 16 | 4.00 |
| 10 | 1 | 2 | 18 | 4.17 |
| 3 | 1 | 3 | 6 | 2.58 |
| 4 | 1 | 3 | 9 | 3.17 |
| 5 | 1 | 3 | 12 | 3.58 |
| 6 | 1 | 3 | 15 | 3.91 |
| 7 | 1 | 3 | 18 | 4.17 Ex #2 |
| 8 | 1 | 3 | 21 | 4.39 |
| 9 | 1 | 3 | 24 | 4.58 |
| 10 | 1 | 3 | 27 | 4.75 |

TABLE 7B

Bits Per Cycle, Two Stop Bases

| # Levels | # Stops | # Stop Types | # Probes | # Bits Per Cycle |
|---|---|---|---|---|
| 3 | 2 | 1 | 1 | 0.00 |
| 4 | 2 | 1 | 3 | 1.58 |
| 5 | 2 | 1 | 6 | 2.58 |
| 6 | 2 | 1 | 10 | 3.32 |
| 7 | 2 | 1 | 15 | 3.91 |
| 8 | 2 | 1 | 21 | 4.39 |
| 9 | 2 | 1 | 28 | 4.31 |
| 10 | 2 | 1 | 36 | 5.17 |
| 3 | 2 | 2 | 4 | 2.00 |
| 4 | 2 | 2 | 12 | 3.58 |
| 5 | 2 | 2 | 24 | 4.53 |
| 6 | 2 | 2 | 40 | 5.32 |
| 7 | 2 | 2 | 60 | 5.91 |
| 8 | 2 | 2 | 84 | 6.39 Ex #4 |
| 9 | 2 | 2 | 112 | 6.81 |
| 10 | 2 | 2 | 144 | 7.17 |
| 3 | 2 | 3 | 9 | 3.17 |
| 4 | 2 | 3 | 27 | 4.75 Ex #3 |
| 5 | 2 | 3 | 54 | 5.75 |
| 6 | 2 | 3 | 90 | 6.49 |
| 7 | 2 | 3 | 135 | 7.08 |
| 8 | 2 | 3 | 189 | 7.56 |
| 9 | 2 | 3 | 252 | 7.98 |
| 10 | 2 | 3 | 324 | 8.34 Ex #5 |

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

All references, issued patents and patent applications cited within the body of the instant specification are hereby incorporated by reference in their entirety, for all purposes.

What is claimed is:

1. A method of detecting a probe bound to a target analyte,
   a. contacting the probe bound to a target analyte with a reaction mixture comprising reagents and under conditions that results in synthesis of a polynucleotide strand using a tail region as a template, wherein the tail region is bound to the probe, and wherein the tail region comprises a first homopolymer region of a first length of at least 25 nucleotides, a second homopolymer region of a second length of at least 25 nucleotides and a stop base between said first homopolymer region and said second homopolymer region that is distinct from the bases within the first homopolymer region and the second homopolymer region, wherein said first homopolymer region and said second homopolymer region differ by at least 25 nucleotides in length; and b. detecting an electrical output signal during synthesis of said polynucleotide thereby detecting said probe bound to said target analyte.

2. The method of claim 1, wherein the ratio of the length of said first homopolymer region to said second homopolymer region is 2:1, 3:1, 4:1, 5:1, 6:1, 7:1, 8:1, 9:1, or 10:1 or the ratio of the length of said second homopolymer region to said first homopolymer region is 2:1, 3:1, 4:1, 5:1, 6:1, 7:1, 8:1, 9:1, or 10:1.

3. The method of claim 2, wherein said tail comprises a 5' end and said 5' end of tail is bound to said probe, said stop base is 3' to said first homopolymer region, and said second homopolymer region is 3' to said stop base.

4. The method of claim 2, wherein said first or second homopolymeric region is at least 100 nucleotides in length.

5. The method of claim 4, wherein said tail comprises a 5' end and said 5' end of tail is bound to said probe and wherein said stop base is 3' to said first homopolymer region and said second homopolymer region is 3' to said stop base.

6. The method of claim 2, wherein the first or second homopolymeric region is at least 200 nucleotides in length.

7. The method of claim 6, wherein said tail comprises a 5' end and said 5' end of tail is bound to said probe and wherein said stop base is 3' to said first homopolymer region and said second homopolymer region is 3' to said stop base.

8. The method of claim 1, wherein said first and second homopolymer regions comprise the same base.

9. The method of claim 1, wherein said first and second homopolymer regions comprise different bases.

10. The method of claim 1, wherein the stop base further comprises a plurality of nucleotides distinct from the bases within the first homopolymer region and the second homopolymer region.

11. The method of claim 1, wherein the tail region is covalently linked to the probe.

12. The method of claim 1, wherein the first or second homopolymer region comprises a poly(dA), poly(dT), poly (dG), poly(dC), poly(A), poly(U), poly(G), or poly(C).

13. The method of claim 1, wherein the analyte is a polypeptide, a protein, or an oligonucleotide.

14. The method of claim 1, wherein the analyte is a small molecule, steroid, or modified nucleic acid.

15. The method of claim 1, wherein said probe comprises an oligonucleotide, a polypeptide, an aptamer, or an antibody.

16. The method of claim 1, wherein said electrical output signal during synthesis is detected by an ion-sensitive field effect transistor (ISFET).

17. The method of claim 1, further comprising detecting a plurality of distinct probes comprising distinct tail regions bound to different target analytes wherein a ratio of said electrical output signal during synthesis of said first and second homopolymer synthesis is different for each distinct probe thereby providing differential detection of each of said different target analytes.

18. The method of claim 17, wherein said tail regions of all said distinct probes are the same length.

19. The method of claim 1, wherein said detecting an electrical output signal during synthesis of said polynucleotide comprises:

(a) contacting said probe with reagents sufficient to cause a first extension of said first homopolymer region as a template and detecting said extension;

(b) contacting said probe with reagents sufficient to cause a second extension of said stop nucleotide as a template;

(c) contacting said probe with reagents sufficient to cause a third extension of said second homopolymer region as a template and detecting said extension; and, (d) comparing the ratio of said first extension to said second extension.

20. The method of claim 1, wherein said probe further comprises a third homopolymer region of a third length of at least 25 nucleotides and a second stop base between said second homopolymer region and said third homopolymer region that is distinct from the bases within said first, second, and third homopolymer regions, wherein each homopolymer region differs by at least 25 nucleotides in length from the other two homopolymer regions.

* * * * *